United States Patent [19]

Adolph

[11] 3,962,349

[45] June 8, 1976

[54] 2,2,2-FLUORODINITROETHYL 2-NITROALKYL ACETALS AND METHODS OF PREPARATION

[75] Inventor: Horst G. Adolph, Beltsville, Md.

[73] Assignee: The United States of America as represented by the Secretary of the Navy, Washington, D.C.

[22] Filed: June 26, 1974

[21] Appl. No.: 483,258

[52] U.S. Cl. ............................. 260/615 A; 149/88; 149/109.4; 252/364; 252/182; 260/614 F
[51] Int. Cl.² ......................................... C07C 43/30
[58] Field of Search .............................. 260/615 A

[56] References Cited
UNITED STATES PATENTS

| | | | |
|---|---|---|---|
| 2,000,252 | 5/1935 | Reppe et al. | 260/615 A |
| 2,780,627 | 2/1957 | Maclean et al. | 260/615 A X |
| 2,853,529 | 9/1958 | Herrmann et al. | 260/615 A |
| 3,024,284 | 3/1962 | Howard et al. | 260/615 A X |
| 3,291,833 | 12/1966 | Gold et al. | 260/615 A |
| 3,629,338 | 12/1971 | Martin | 260/615 A |

FOREIGN PATENTS OR APPLICATIONS

| | | | |
|---|---|---|---|
| 592,972 | 2/1960 | Canada | 260/615 A |
| 939,029 | 10/1963 | United Kingdom | 260/615 A |

Primary Examiner—Howard T. Mars
Attorney, Agent, or Firm—R. S. Sciascia; J. A. Cooke; R. D. Johnson

[57] ABSTRACT

Unsymmetrical nitro and fluoronitro acetals of the formulas

ROCH(CH$_3$)OR' wherein R ≠ R', but wherein both R and R' are selected from the group consisting of
-CH$_2$CXY(NO$_2$), -CH$_2$C(NO$_2$)$_2$CH$_3$,
-CH$_2$CUVCXY(NO$_2$), and
-CH$_2$CUVCWZCXY(NO$_2$), wherein X and Y vary independently and are selected from the group consisting of F and NO$_2$, and wherein U, V, W, and Z vary independently and are selected from the group consisting of H, F, and NO$_2$, are useful as energetic plasticizers in rocket propellants or explosives.

4 Claims, No Drawings

2,2,2-FLUORODINITROETHYL 2-NITROALKYL ACETALS AND METHODS OF PREPARATION

BACKGROUND OF THE INVENTION

This invention relates to acetals and more particularly to acetals containing polynitro or fluoronitro alkyl groups.

Compounds used as plasticizers in propellants and explosives should have low melting points, high boiling points, and high explosive energy content. It was known in the prior art that $NO_2$ groups raise the boiling point and increase the energy content of symmetrical acetals. Unfortunately, $NO_2$ groups also raise the melting points of acetals, making them less suitable as plasticizers.

SUMMARY OF THE INVENTION

Accordingly, one object of this invention is to provide novel energetic explosive compounds.

Another object of this invention is to provide unsymmetrical polynitro and fluoronitro acetals.

A further object of this invention is to provide a process for preparing unsymmetrical polynitro and fluoronitro acetals.

Still another object of this invention is to provide energetic explosive and propellant plasticizers having low melting points but high energy content.

These and other objects of this invention are accomplished by providing unsymmetrical acetals of the formula $$ROCH(CH_3)OR'$$

which are formed by contacting a nitro or fluoronitro vinyl ether of the formula $$ROCH=CH_2,$$

a nitro or fluoronitro alcohol of the formula $$R'OH,$$

and a Lewis acid catalyst, wherein $R \neq R'$, but wherein both R and R' are selected from the group consisting of
-$CH_2CXY(NO_2)$, -$CH_2C(NO_2)_2CH_3$,
-$CH_2CUVCXY(NO_2)$ and
-$CH_2CUVCWZCXY(NO_2)$,
wherein X and Y vary independently and are selected from the group consisting of F and $NO_2$, and wherein U, V, W, and Z vary independently and are selected from the group consisting of H, F, and $NO_2$.

DESCRIPTION OF THE PREFERRED EMBODIMENT

The plasticizers of the instant invention represented by the formula $$ROCH(CH_3)OR'$$

wherein R and R' have hereinbefore defined can be prepared by the following chemical reaction:

$$ROCH=CH_2 + R'OH \xrightarrow{\text{Lewis acid}} ROCH(CH_3)OR'.$$

The preferred unsymmetrical acetals have the formula $$ROCH(CH_3)OR'$$

wherein $R \neq R'$, but wherein both R and R' are selected from the group consisting of -$CH_2CXY(NO_2)$, —$CH_2C(NO_2)_2CH_3$, and -$CHC(NO_2)_2CH_2CF(NO_2)_2$ wherein X and Y vary independently and are selected from the group consisting of F and $NO_2$. The more preferred unsymmetrical acetals are
$CF(NO_2)_2CH_2OCH(CH_3)OCH_2F_2(NO_2)$,
$CF(NO_2)_2CH_2OCH(CH_3)OCH_2C(NO_2)_3$,
$CF(NO_2)_2CH_2OCH(CH_3)OCH_2C(NO_2)_2CH_3$,
and
$CF(NO_2)_2CH_2OCH(CH_3)OCH_2C(NO_2)_2CH_2CF(NO_2)_2$.

The vinyl ether which is used may be selected from the group consisting of
$CXY(NO_2)CH_2OCH=CH_2$,
$CH_3C(NO_2)_2CH_2OCH=CH_2$,
$CXY(NO_2)CUVCH_2OCH=CH_2$, and
$CXY(NO_2)CUVCWZCH_2OCH=CH_2$,
wherein X and Y vary independently and are selected from the group consisting of F and $NO_2$, and U, V, W, and Z vary independently and are selected from the group consisting of F, H, and $NO_2$. For example, vinyl ethers such as the following may be used to synthesis the acetals of the present invention:
$CF_2(NO_2)CH_2OCH=CH_2$,
$CF(NO_2)_2CH_2OCH=CH_2$,
$C(NO_2)_3CH_2OCH=CH_2$,
$CH_3C(NO_2)_2CH_2OCH=CH_2$,
$CF_2(NO_2)CH_2CH_2OCH=CH_2$,
$CF(NO_2)_2CH_2CH_2OCH=CH_2$,
$C(NO_2)_3CH_2CH_2OCH=CH_2$,
$CF_2(NO_2)CF(NO_2)CH_2OCH=CH_2$,
$CF(NO_2)_2CF(NO_2)CH_2OCH=CH_2$,
$C(NO_2)_3CF(NO_2)CH_2OCH=CH_2$,
$CF_2(NO_2)C(NO_2)_2CH_2OCH=CH_2$,
$CF(NO_2)_2C(NO_2)_2CH_2OCH=CH_2$,
$C(NO_2)_3C(NO_2)_2CH_2OCH=CH_2$,
$CF_2(NO_2)CH_2CH_2CH_2OCH=CH_2$,
$CF_2(NO_2)CH_2CH(NO_2)CH_2OCH=CH_2$,
$CF_2(NO_2)CH_2CF(NO_2)CH_2OCH=CH_2$,
$CF_2(NO_2)CH_2C(NO_2)_2CH_2OCH=CH_2$,
$CF_2(NO_2)CF(NO_2)C(NO_2)_2CH_2OCH=CH_2$,
$CF(NO_2)_2CH_2C(NO_2)_2CH_2OCH=CH_2$,
$CF(NO_2)_2CF_2C(NO_2)_2CH_2OCH=CH_2$,
$CF(NO_2)_2C(NO_2)_2C(NO_2)_2CH_2OCH=CH_2$,
$C(NO_2)_3CH_2C(NO_2)_2CH_2OCH=CH_2$,
etc.

The alcohol which is used may be selected from the group consisting of
$CXY(NO_2)CH_2OH, CH_3C(NO_2)_2CH_2OH$,
$CXY(NO_2)CUVCH_2OH$, and
$CXY(NO_2)CUVCWZCH_2OH$,
wherein X and Y vary independently and are selected from the group consisting of F and $NO_2$, and U, V, W, and Z vary independently and are selected from the group consisting of H, F, and $NO_2$. For instance, alcohols such as the following may be used in the synthesis of the acetals of the present invention:
$CF_2(NO_2)CH_2OH$,
$CF(NO_2)_2CH_2OH$,
$C(NO_2)_3CH_2OH$,
$CH_3C(NO_2)_2CH_2OH$,
$CF_2(NO_2)CH_2CH_2OH$,
$CF_2(NO_2)CH(NO_2)CH_2OH$,
$CF_2(NO_2)C(NO_2)_2CH_2OH$,
$CF_2(NO_2)CF(NO_2)CH_2OH$,
$CF(NO_2)_2CH_2CH_2OH$, $CF(NO_2)_2C(NO_2)_2CH_2OH$,
$C(NO_2)_3CH_2CH_2OH$,
$CF_2(NO_2)_3CH_2C(NO_2)_2CH_2OH$,
$CF_2(NO_2)CF(NO_2)C(NO_2)_2CH_2OH$,
etc.

The reaction temperature affects not only the rate of reaction but also the purity of the unsymmetrical acetal product. The higher the reaction temperature the faster the reaction, but also the greater the percentage of symmetrical acetals which will contaminate the product. On the other hand, if too low a temperature is selected, the reaction may take too long to be practical. In general, from about −20°C to about +20° is the preferred temperature range with from −5°C to 5°C being the more preferred temperature range.

A Lewis acid such as $BF_3$ or $FeCl_3$ catalyzes the reaction. The amount of catalyst used will affect both the rate of reaction and the purity of the final product. If not enough catalyst is used the reaction will be too slow to be practical. Contrarily, if too much catalyst is used the reaction will yield an unsymmetrical acetal which is heavily contaminated with symmetrical acetals which are formed by side reactions.

Note that after the reaction the produce must be washed to remove the Lewis acid. If this is not done the product will be unstable at higher temperature because the Lewis acid will catalyze the conversion of the unsymmetrical acetal into the symmetrical acetals. If approximately equilmolar amounts of the vinyl ether and the alcohol are contacted at a temperature within the more preferred range of −5°C to +5°C and if an effective amount of Lewis acid catalyst is added, the product will be a mixture comprising from more than 90 to less than 100 percent by weight of the unsymmetrical acetal, $ROCH(CH_3)OR'$, with the two corresponding symmetrical acetals, $ROCH(CH_3)OR$ and $R'OCH(CH_3)OR'$, constituting the remainder of the product. A molar ratio of the Lewis acid catalyst to the reactants of from abrout 1:8 to about 1:12 is an appropriate amount. Mixtures of unsymmetrical and symmetrical acetals in which the unsymmetrical acetal comprises more than 90 percent of mixture have melting points as low as or lower than the pure unsymmetrical acetal. (Melting point in this case means the lowest temperature at which the acetal mixture is completely converted from the solid to the liquid phase.) The low melting point of mixtures having more than 90 but less than 100 weight percent of the unsymmetrical acetal is important because the separation of the unsymmetrical acetal from its corresponding symmetrical acetals is extremely difficult to accomplish in the laboratory and virtually impossible on an industrial scale.

Lastly, any inert organic solvent which is capable of dissolving the reactants and the catalyst without interferring with the reaction is suitable as a reaction medium. For example methylene chloride, ethylene chloride, chloroform, and similar compounds are suitable.

To more clearly illustrate this invention, the following examples are presented. It should be understood, however, that these examples are presented merely as a means of illustration and are not intended to limit the scope of the invention in any way.

EXAMPLE 1

2-fluoro-2,2-dinitroethyl 2,2-difluoro-2-nitroethyl acetal

A solution of 0.1 moles of 2-fluoro-2,2-dinitroethyl vinyl ether and 0.1 moles of 2,2-difluoro-2-nitroethanol in 100 ml of ethylene chloride was dried by adding 5A molecular sieves and then cooled to about 0°C in an ice bath. 1 ml. of boron trifluoride etherate was added dropwise and the mixture was stirred for 6 hours, with continued ice-cooling. The molecular sieves were than filtered out of the methylene chloride solution. The solution was washed with water and then with dilute sodium bicarbonate solution, dried over magnesium sulfate, and then filtered to remove the magnesium sulfate. Removal of the solvents in vacuo left the product as a colorless oil with a melting point of under −25°C.

Calculated for $C_6H_6N_3O_8F_3$ (weight percent): N, 13.68; F, 18.56. Found (weight percent): N, 13.90; F, 18.48.

NMR($CDCl_3$). $\delta$ 5.00 q ($J_{HH}$ 5 CPS); $\delta$ 4.57 d ($J_{HF}$ 18 CPS); $\delta$ 4.21 t ($J_{HF}$ 9 CPS); $\delta$ 1.36 d ($J_{HH}$ 5 CPS).

EXAMPLE 2

2-fluoro-2,2-dinitroethyl 2,2,2-trinitroethyl acetal

The procedure of Example 1 was used to react 0.1 moles 2-fluoro-2,2-dinitroethyl vinyl ether with 0.1 moles of 2,2,2-trinitroethanol. The product, 2-fluoro-2,2-dinitroethyl 2,2,2-trinitroethyl acetal, was a pale yellow oil having a melting point of 3°–4°C. ANALYSIS: Calculated for $C_6H_8FN_5O_{12}$ (weight percent): F, 5.26; N, 19.39. Found (weight percent): F, 5.50: N, 19.29. NMR ($CDCl_3$). $\delta$ 5.09 q ($J_{HH}$ 5 CPS); $\delta$ 4.73 S; $\delta$ 4.61 d ($J_{HF}$ 18 CPS); $\delta$ 1.43 d ($J_{HH}$ 5 CPS).

EXAMPLE 3

2-fluoro-2,2-dinitroethyl 2,2-dinitropropyl acetal

The procedure of Example 1 was used to react 0.1 moles of 2-fluoro-2,2-dinitroethyl vinyl ether with 0.1 moles of 2,2-dinitropropanol. The product, 2-fluoro-2,2-dinitroethyl 2,2-dinitropropyl acetal, was a colorless oil. ANALYSIS: Calculated for $C_7H_{11}FN_4O_{10}$ (weight percent): F, 5.76; N, 16.97. Found (weight percent): F, 5.81; N, 17.20. NMR ($CDCl_3$). $\delta$ 5.01 q ($J_{HH}$ 6 CPS); $\delta$ 4.52 d ($J_{HF}$ 18 CPS); $\delta$ 4.26 S; $\delta$ 2.18 S; $\delta$ 1.38 d ($J_{HH}$ 6 CPS).

EXAMPLE 4

2-fluoro-2,2-dinitroethyl 4-fluoro-2,2,4,4-tetranitrobutyl acetal

The procedure of Example 1 was used to react 0.1 moles of 2-fluoro-2,2-dinitroethyl vinyl ether with 0.1 moles of 4-fluoro-2,2,4,4-tetranitrobutanol. The product 2-fluoro-2,2-dinitroethyl 4-fluoro-2,2,4,4-tetranitrobutyl acetal which was a viscuous, colorless liquid. ANALYSIS: Calculated for $C_8H_{10}F_2N_6O_{14}$ (weight percent): F, 8.41; N, 18.59. Found (weight percent): F, 8.69; N, 18.50. NMR($CDCl_3$). $\delta$ 5.05 q ($J_{HH}$ 6 CPS); $\delta$ 4.40 – 4.80 (series of overlapping multiplets and singlets due to $CF(NO_2)_2CH_2O-$, and $CF(NO_2)_2CH_2C(NO_2)_2CH_2O-$); $\delta$ 1.40 d ($J_{HH}$ 6 CPS).

I claim:

1. A compound having the formula $ROCH(CH_3)OR'$ wherein $R \neq R'$, but wherein both R and R' are selected from the group consisting of $-CH_2CXY(NO_2)$, $-CH_2C(NO_2)_2CH_3$ and $-CH_2C(NO_2)_2CH_2CF(NO_2)_2$ wherein X and Y vary independently and are selected from the group consisting of F and $NO_2$.

2. A compound according to claim 1 which is selected from the group consisting of
$CF(NO_2)_2CH_2OCH(CH_3)OCH_2CF_2(NO_2)$,
$CF(NO_2)_2CH_2OCH(CH_3)OCH_2C(NO_2)_3$,
$CF(NO_2)_2CH_2OCH(CH_3)OCH_2C(NO_2)_2CH_3$, and $CF(NO_2)_2CH_2OCH(CH_3)OCH_2C(NO_2)_2CH_2CF(NO_2)_2$.

3. A compound according to claim 2 wherein the compound is:

$CF(NO_2)_2CH_2O\text{-}CH(CH_3)\text{-}OCH_2C(NO_2)_3$.

4. A compound according to claim 2 wherein the compound is:

$CF_2(NO_2)CH_2OCH(CH_3)OCH_2CF(NO_2)_2$.

* * * * *